(12) United States Patent
Rocco et al.

(10) Patent No.: US 10,823,700 B2
(45) Date of Patent: Nov. 3, 2020

(54) ACTIVE OIL DEBRIS MONITOR PARTICLE DETECTION AND MONITORING SYSTEM

(71) Applicant: United Technologies Corporation, Farmington, CT (US)

(72) Inventors: Edward Thomas Rocco, Rocky Hill, CT (US); Sheridon Everette Haye, Mansfield, CT (US)

(73) Assignee: Raytheon Technologies Corporation, Farmington, CT (US)

( * ) Notice: Subject to any disclaimer, the term of this patent is extended or adjusted under 35 U.S.C. 154(b) by 59 days.

(21) Appl. No.: 16/277,186

(22) Filed: Feb. 15, 2019

(65) Prior Publication Data

US 2020/0264135 A1 Aug. 20, 2020

(51) Int. Cl.
*G01N 27/74* (2006.01)
*G01N 33/28* (2006.01)

(52) U.S. Cl.
CPC ......... *G01N 27/74* (2013.01); *G01N 33/2858* (2013.01)

(58) Field of Classification Search
CPC ........... G01N 33/2858; G01N 33/2835; G01N 27/74; G01N 15/0656
See application file for complete search history.

(56) References Cited

U.S. PATENT DOCUMENTS

| | | |
|---|---|---|
| 5,061,070 A | 10/1991 | Batchelder et al. |
| 5,315,243 A * | 5/1994 | Kempster .......... G01N 15/0656 324/204 |
| 6,051,970 A | 4/2000 | Hutchings |
| 6,377,052 B1 | 4/2002 | McGinnis et al. |
| 6,459,995 B1 | 10/2002 | Collister |
| 6,839,620 B1 | 1/2005 | Koehler et al. |
| 6,850,865 B2 | 2/2005 | Hirthe et al. |
| 6,984,986 B2 | 1/2006 | Sosnowski et al. |
| 6,989,680 B2 | 1/2006 | Sosnowski et al. |
| 7,043,402 B2 | 5/2006 | Phillips et al. |
| 7,581,434 B1 | 9/2009 | Discenzo et al. |
| 7,956,601 B2 | 6/2011 | Becker et al. |
| 7,983,864 B2 | 7/2011 | Hu et al. |
| 8,340,928 B2 | 12/2012 | Sun |
| 8,826,741 B2 | 9/2014 | Kuehl et al. |

(Continued)

FOREIGN PATENT DOCUMENTS

CN 103217366CN A 7/2013

OTHER PUBLICATIONS

EP Search Report dated Aug. 3, 2020, issued for corresponding European Patent Application No. 20157772.3.

*Primary Examiner* — Jay Patidar
(74) *Attorney, Agent, or Firm* — Bachman & LaPointe, P.C.

(57) ABSTRACT

A method for determining the presence of a particle while actively calculating and monitoring oil debris monitor phase angle in an oil system including collecting I and Q channel data from an oil debris monitor sensor; determining whether the I and Q data is symmetric; processing the I and Q channel data to identify a ferrous and nonferrous signal in response to the I and Q data being symmetric; processing the ferrous and nonferrous signals to determine if a particle is present; determining a symmetry factor from the I and Q channel data in response to the particle being present and confirming that the particle is present from the symmetry factor.

19 Claims, 20 Drawing Sheets

(56) References Cited

U.S. PATENT DOCUMENTS

| | | |
|---|---|---|
| 9,354,094 B2 | 5/2016 | Sinha |
| 2009/0051350 A1 | 2/2009 | Becker et al. |
| 2010/0109686 A1 | 5/2010 | Zhe et al. |
| 2015/0343346 A1 | 12/2015 | Sheridan |
| 2017/0138217 A1 | 5/2017 | Schwarz et al. |
| 2017/0350842 A1 | 12/2017 | Mohr et al. |
| 2018/0023414 A1 | 1/2018 | Hagen et al. |
| 2018/0135455 A1 | 5/2018 | Khibnik et al. |
| 2018/0266938 A1 | 9/2018 | Chow |

* cited by examiner

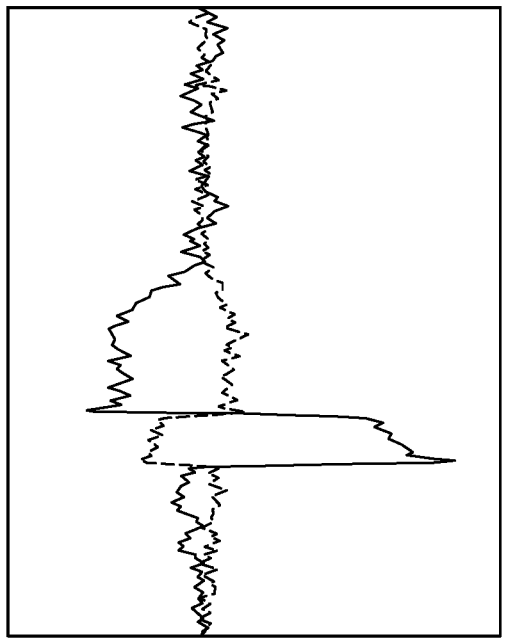
FIG. 24
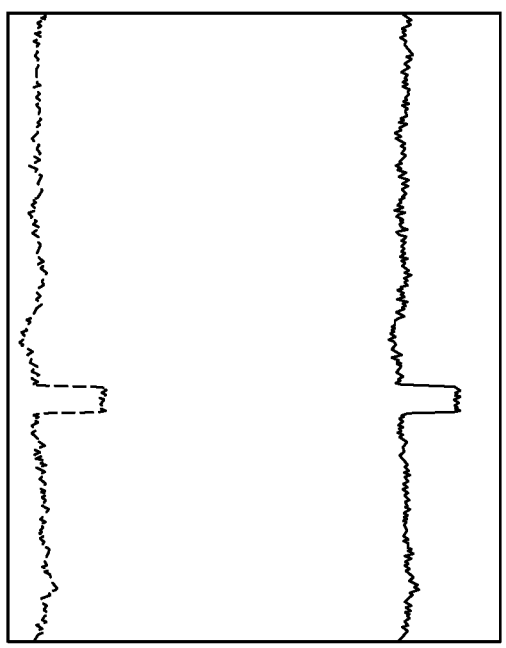
FIG. 23
| Fe Sym Factor | I Sym Factor | Q Sym Factor |
|---|---|---|
| 2.1 | 22.7 | 14.5 |
FIG. 25

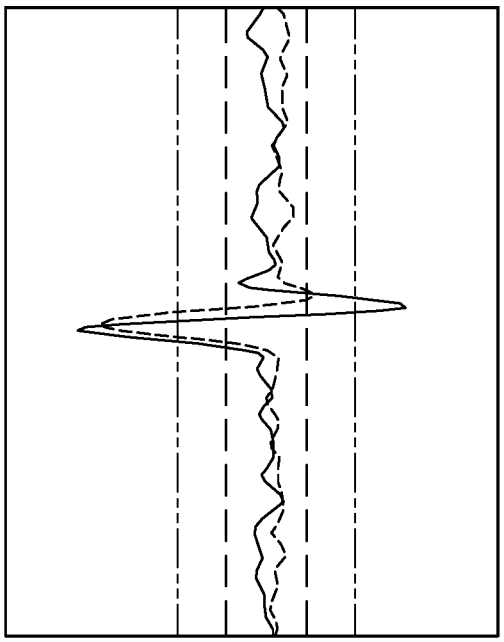
FIG. 27
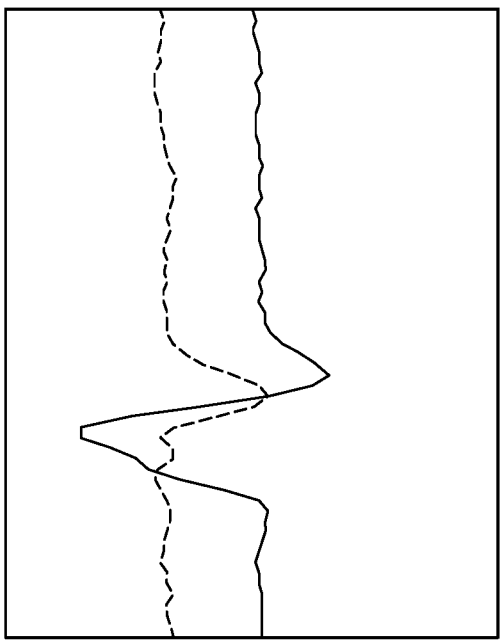
FIG. 26
| Fe Sym Factor | I Sym Factor | Q Sym Factor |
|---|---|---|
| 1.4 | 2.5 | 33.2 |
FIG. 28

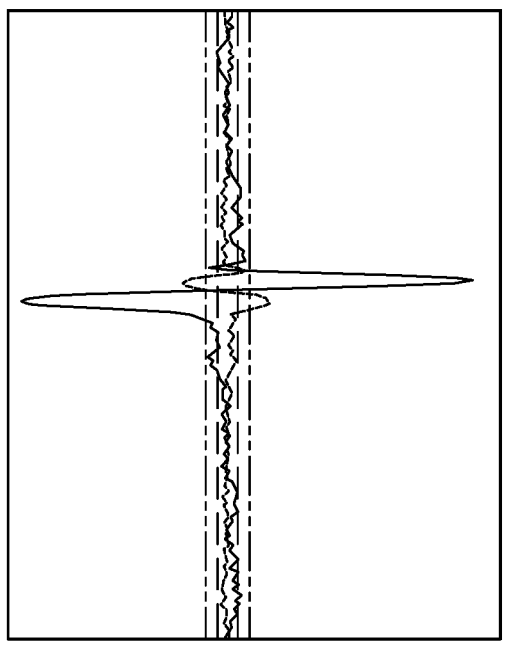
FIG. 30
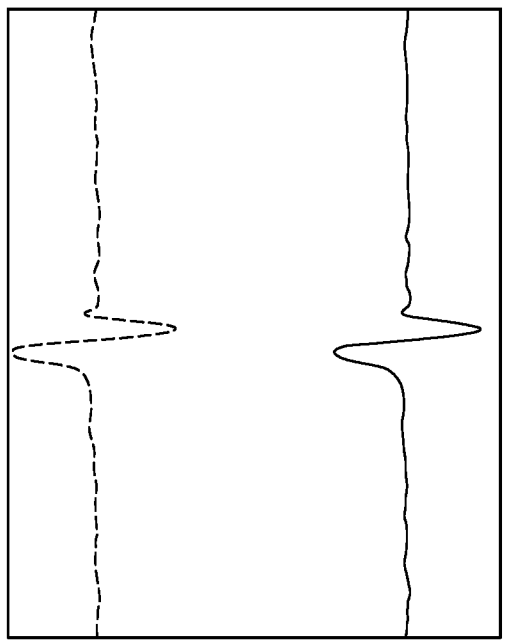
FIG. 29
| Fe Sym Factor | I Sym Factor | Q Sym Factor |
|---|---|---|
| 1.2 | 1.0 | 1.1 |
FIG. 31

ACTIVE OIL DEBRIS MONITOR PARTICLE DETECTION AND MONITORING SYSTEM

BACKGROUND

The present disclosure relates to an oil system for a gas turbine engine and, more particularly, to an on-board system to confirm whether or not a particle detection is valid.

Many types of mechanical machinery include various components that require lubrication. For example, gas turbine engines typically have gears and bearings that require a lubricating liquid, such as oil, to lubricate and cool those gears and bearings during operation. During operation, debris accumulates in the lubricating liquid. Because of this, lubrication systems typically include an oil debris monitor system to sense metal debris in the oil. An oil debris monitor system is normally used to flag the initiation or progression of mechanical failures in the lubricated mechanical machinery.

It is extremely difficult to validate the accuracy of an oil debris monitor system while it is installed in a lubrication system. Thus, it is important to validate the accuracy of an oil debris monitor prior to it being installed in the lubrication system. It can also be difficult to reliably validate accuracy of an oil debris monitor in a lab with known validation methods, especially in a lab that does not allow oil to be present. An oil debris monitor phase angle is often used to classify detected particle types (ferrous/nonferrous) through a mathematical transformation. Currently, the phase angle is hardcoded into the system. The phase angle is determined by an offline calibration test process and the resultant value calculated. In legacy systems, the phase angle applied to oil debris monitor data for particle detection is a fixed value in the software. However, the proper phase angle for an individual oil debris monitor is a function of system capacitance and inductance, so every oil debris monitor sensor phase angle is different and can change based on system condition and related system components. The use of an improper phase angle can reduce the system capability to detect particles and can also lead to particle type and size misclassification. Furthermore, a system phase angle should be fixed, and any sudden changes or instability in phase angle may be indicative of system deterioration.

Analysis of ODM system raw data requires human expertise to confirm whether or not a particle detection is valid. It is possible that in a noisy system, the background noise signature can generate a particle count, even if the shape, by visual inspection, is not particle like.

SUMMARY

A method for determining the presence of a particle while actively calculating and monitoring oil debris monitor phase angle in an oil system according to one disclosed non-limiting embodiment of the present disclosure includes: a) collecting I and Q channel data from an oil debris monitor sensor; b) determining whether the I and Q data is symmetric; c) processing the I and Q channel data to identify a ferrous and nonferrous signal in response to the I and Q data being symmetric in step b); d) processing the ferrous and nonferrous signals to determine if a particle is present; e) determining a symmetry factor from the I and Q channel data in response to the possibility that the particle is present in step d); and f) confirming that the particle is present from the symmetry factor.

A further embodiment of any of the foregoing embodiments of the present disclosure includes that step b) comprises determining if the lobe peaks are symmetric.

A further embodiment of any of the foregoing embodiments of the present disclosure includes that the ferrous and nonferrous signals are used for detection.

A further embodiment of any of the foregoing embodiments of the present disclosure includes that said step d) comprises filtering and phase adjusting the ferrous and nonferrous signals.

A further embodiment of any of the foregoing embodiments of the present disclosure includes continually filling a buffer of the controller with the I and Q channel data.

A further embodiment of any of the foregoing embodiments of the present disclosure includes converting the I and Q channel data to digital I and Q data within the controller on-board an aircraft.

A further embodiment of any of the foregoing embodiments of the present disclosure includes locating the oil debris monitor sensor within an oil supply path.

A further embodiment of any of the foregoing embodiments of the present disclosure includes locating the oil debris monitor sensor within an oil return path.

A further embodiment of any of the foregoing embodiments of the present disclosure includes that the symmetry factor=peak/absolute value (valley) of the I and Q channel data.

A further embodiment of any of the foregoing embodiments of the present disclosure includes that the particle is rejected in response to the symmetry factor being less than a threshold.

A further embodiment of any of the foregoing embodiments of the present disclosure includes that the example threshold is 1-4.

A further embodiment of any of the foregoing embodiments of the present disclosure includes that the symmetry factor is applied to the I channel data.

A further embodiment of any of the foregoing embodiments of the present disclosure includes that the symmetry factor is applied to the Q channel data.

An oil system for a gas turbine engine according to one disclosed non-limiting embodiment of the present disclosure includes: an oil flow path; an in-line oil debris monitor sensor; and a control system in communication with the in-line oil debris monitor sensor to determine whether a particle is present from a symmetry factor of the I and Q channel data.

A further embodiment of any of the foregoing embodiments of the present disclosure includes that the oil flow path is in communication with a geared architecture of the gas turbine engine.

A further embodiment of any of the foregoing embodiments of the present disclosure includes that the oil flow path is an oil supply path.

A further embodiment of any of the foregoing embodiments of the present disclosure includes that the oil flow path is an oil return path.

A further embodiment of any of the foregoing embodiments of the present disclosure includes a chip collector within the oil flow path.

A further embodiment of any of the foregoing embodiments of the present disclosure includes that the control system comprises a controller on-board an aircraft.

The foregoing features and elements may be combined in various combinations without exclusivity, unless expressly indicated otherwise. These features and elements as well as the operation thereof will become more apparent in light of the following description and the accompanying drawings. It should be appreciated; however, the following description and drawings are intended to be exemplary in nature and non-limiting.

BRIEF DESCRIPTION OF THE DRAWINGS

Various features will become apparent to those skilled in the art from the following detailed description of the disclosed non-limiting embodiments. The drawings that accompany the detailed description can be briefly described as follows:

FIG. 23 is a graphical representation of the I and Q channel data according to one embodiment.

FIG. 24 is a graphical representation of the I and Q channel data converted into ferrous and nonferrous signal data.

FIG. 25 is a table representative of the symmetry check to provides an additional validity check for candidate particles.

FIG. 26 is a graphical representation of the I and Q channel data according to another embodiment.

FIG. 27 is a graphical representation of the I and Q channel data converted into ferrous and nonferrous signal data.

FIG. 28 is a table representative of the symmetry check to provides an additional validity check for candidate particles.

FIG. 29 is a graphical representation of the I and Q channel data according to another embodiment.

FIG. 30 is a graphical representation of the I and Q channel data converted into ferrous and nonferrous signal data.

FIG. 31 is a table representative of the symmetry check to provides an additional validity check for candidate particles.

DETAILED DESCRIPTION

Figure 1:
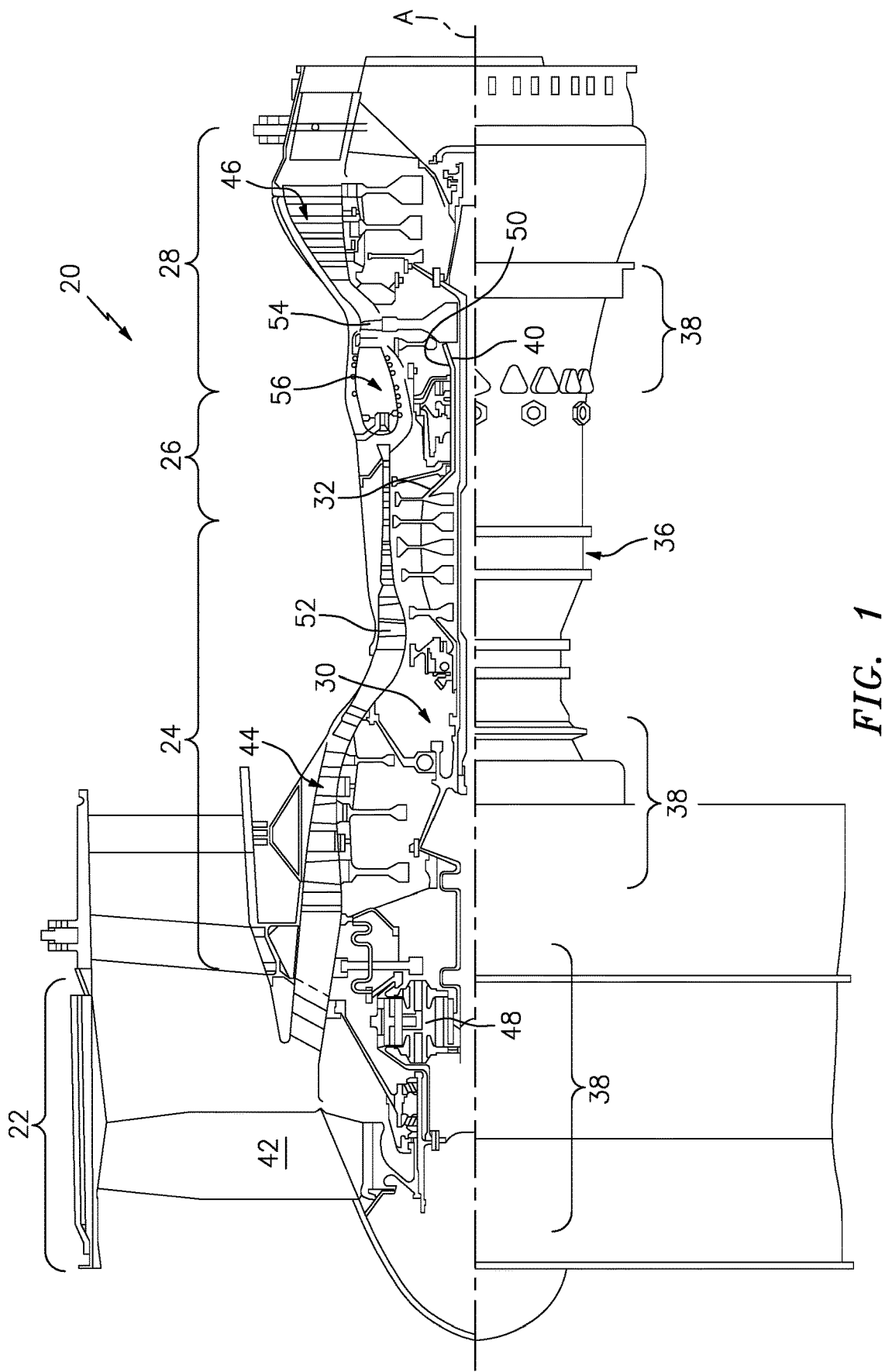
FIG. 1 is a schematic cross-section of an example gas turbine engine architecture.

FIG. 1 schematically illustrates a gas turbine engine 20. The gas turbine engine 20 is disclosed herein as a two-spool turbofan that generally incorporates a fan section 22, a compressor section 24, a combustor section 26, and a turbine section 28. The fan section 22 drives air along a bypass flowpath while the compressor section 24 drives air along a core flowpath for compression and communication into the combustor section 26, then expansion through the turbine section 28. Although depicted as a turbofan in the disclosed non-limiting embodiment, it should be appreciated that the concepts described herein may be applied to other engine architectures such as turbojets, turboshafts, and three-spool (plus fan) turbofans.

The engine 20 generally includes a low spool 30 and a high spool 32 mounted for rotation about an engine central longitudinal axis X relative to an engine static structure 36 via several bearings 38. The low spool 30 generally includes an inner shaft 40 that interconnects a fan 42, a low pressure compressor ("LPC") 44 and a low pressure turbine ("LPT") 46. The inner shaft 40 drives the fan 42 directly or through a geared architecture 48 that drives the fan 42 at a lower speed than the low spool 30. An exemplary reduction transmission is an epicyclic transmission, such as a planetary or star gear system.

The high spool 32 includes an outer shaft 50 that interconnects a high pressure compressor ("HPC") 52 and high pressure turbine ("HPT") 54. A combustor 56 is arranged between the high pressure compressor 52 and the high pressure turbine 54. The inner shaft 40 and the outer shaft 50 are concentric and rotate about the engine central longitudinal axis X which is collinear with their longitudinal axes.

Core airflow is compressed by the LPC 44, then the HPC 52, mixed with the fuel and burned in the combustor 56, then expanded over the HPT 54 and the LPT 46 which rotationally drive the respective high spool 32 and the low spool 30 in response to the expansion. The shafts 40, 50 are supported at a plurality of points by bearings 38 within the static structure 36.

Figure 2:
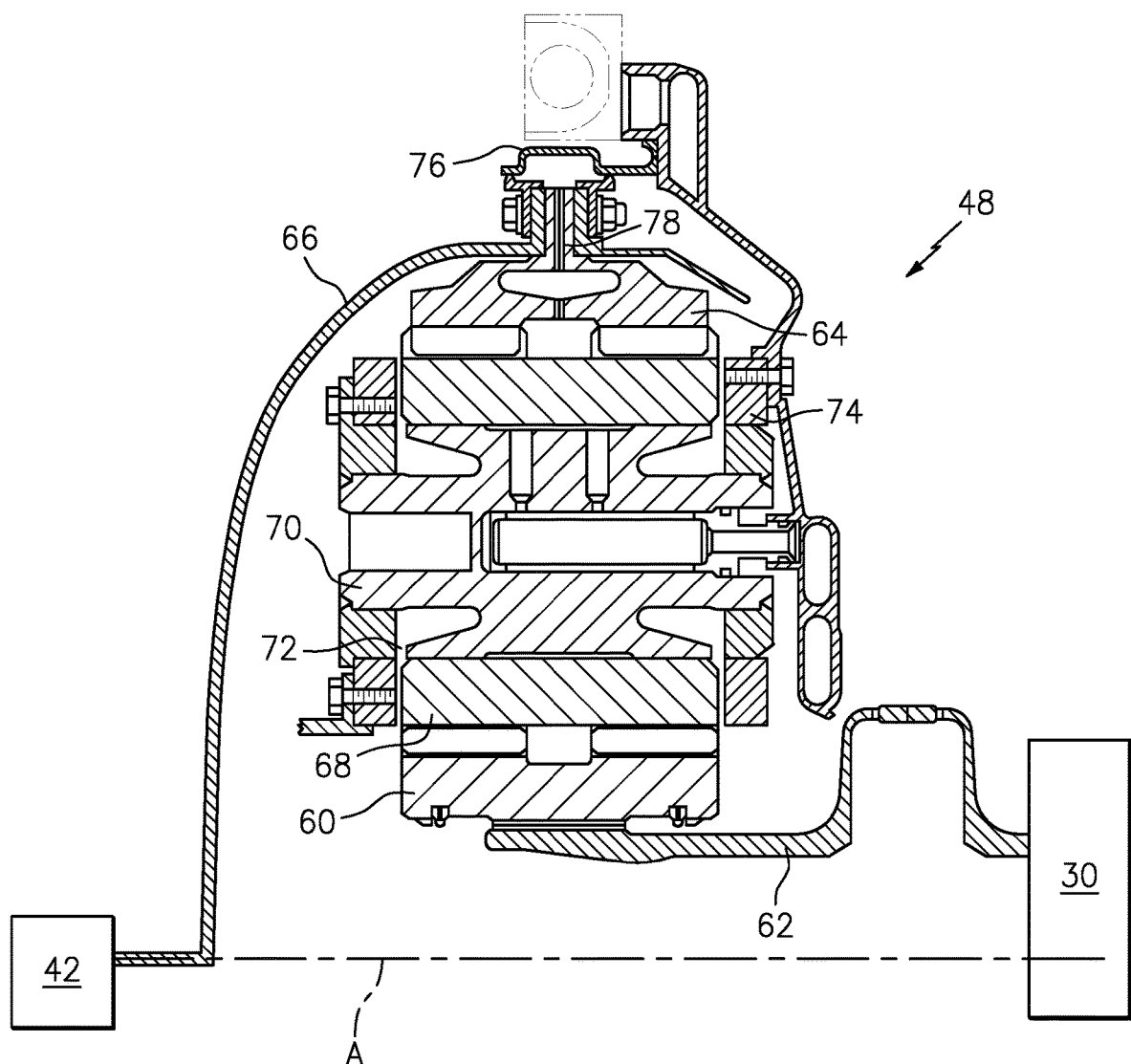
FIG. 2 is a schematic cross-section of a geared architecture for a gas turbine engine.

With reference to FIG. 2, the geared architecture 48 includes a sun gear 60 driven by a sun gear input shaft 62 from the low spool 30, a ring gear 64 connected to a ring gear output shaft 66 to drive the fan 42 and a set of intermediate gears 68 in meshing engagement with the sun gear 60 and ring gear 64. Each intermediate gear 68 is mounted about a journal pin 70 which are each respectively supported by a carrier 74. The input shaft 62 and the output shaft 66 counter-rotate as the sun gear 60 and the ring gear 64 are rotatable about the engine central longitudinal axis A. The carrier 74 is grounded and non-rotatable even though the individual intermediate gears 68 are each rotatable about their respective axes 80. An oil recovery gutter 76 is located around the ring gear 64. The oil recovery gutter 76 may be radially arranged with respect to the engine central longitudinal axis A.

A replenishable film of oil, not shown, is supplied to an annular space 72 between each intermediate gear 68 and the respective journal pin 70. One example applicable oil meets U.S. Military Specification MIL-PRF-23699, for example, Mobil Jet Oil II manufactured by ExxonMobil Aviation, United States. Oil is supplied through the carrier 74 and into each journal pin 70 to lubricate and cool the gears 60, 64, 68 of the geared architecture 48. Once communicated through the geared architecture 48 the oil is radially expelled through the oil recovery gutter 76 in the ring gear 64 by various paths such as oil passage 78.

Figure 3:
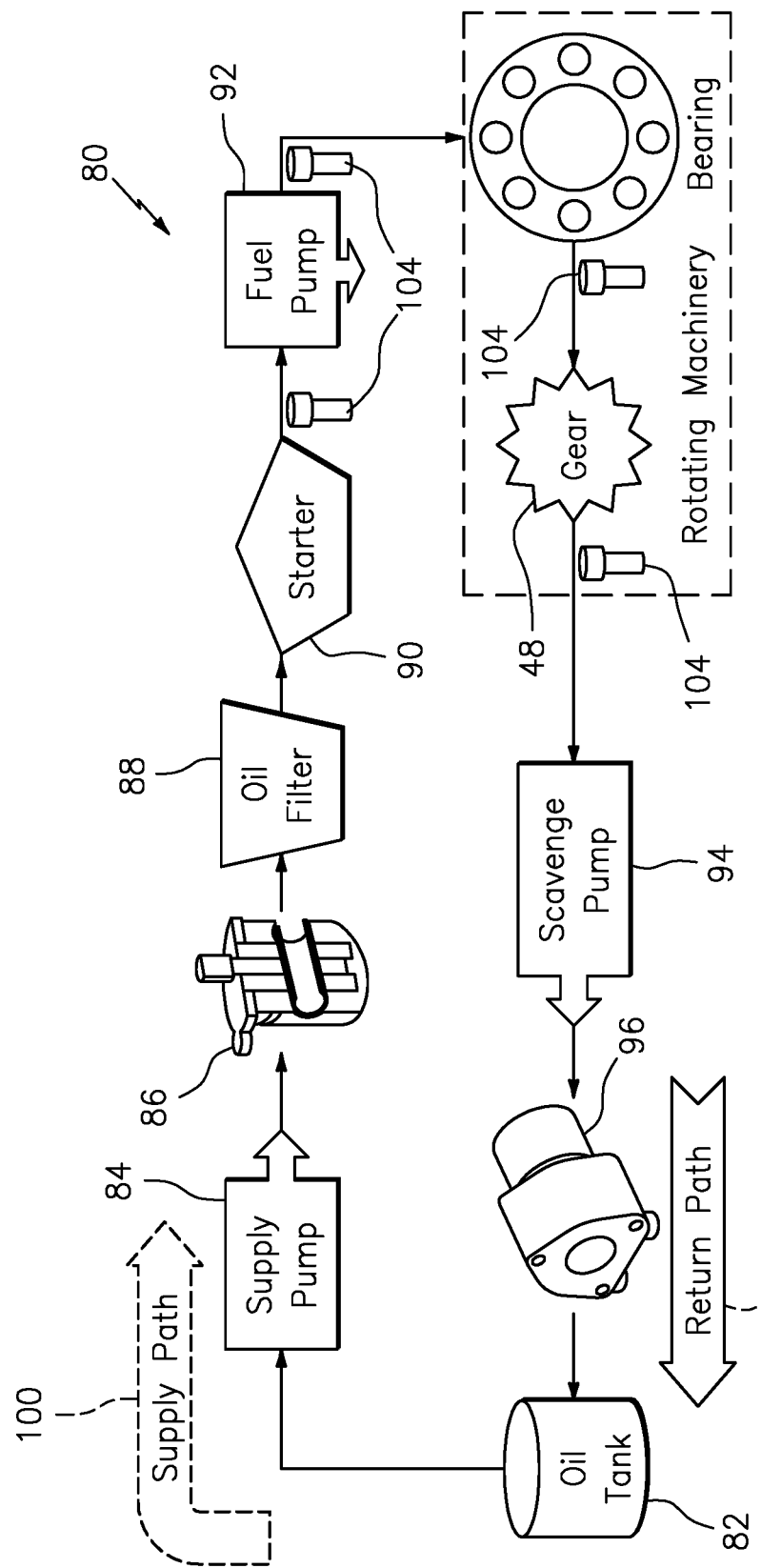
FIG. 3 is a schematic diagram of an oil system for a geared architecture gas turbine engine.

With reference to FIG. 3, an oil system 80 is schematically illustrated in block diagram form for the geared architecture 48 as well as other components which receive oil. It should be appreciated that the oil system 80 is but a schematic illustration and is simplified in comparison to an actual oil system. The oil system 80 generally includes an oil tank 82, a supply pump 84, a sensor 86, an oil filter 88, a starter 90, a fuel pump 92, the geared architecture 48, the scavenge pump 94, and a sensor 96. The oil flow to the geared architecture 48 may be considered an oil supply path 100, and the oil flow from the geared architecture 48 can be considered an oil return path 102. A multiple of chip collectors 104 may be located in the supply path 100 and the return path 102 to capture ferrous debris.

The sensors 86, 96 may utilize two outer field coils to generate a drive signal (high frequency cyclic signal), causing equal and opposing magnetic fields (M-field). The ferrous particle strength of the M-field created by one field coil after another, causes the processed signal to be a period of a sine wave. The nonferrous particle weakens the M-field created by one field coil after another, causing the similar sine wave but in opposing polarity. Generally, the signal magnitude is proportional to the size of particle and the signal width is inversely proportional to the particle speed.

Figure 4:
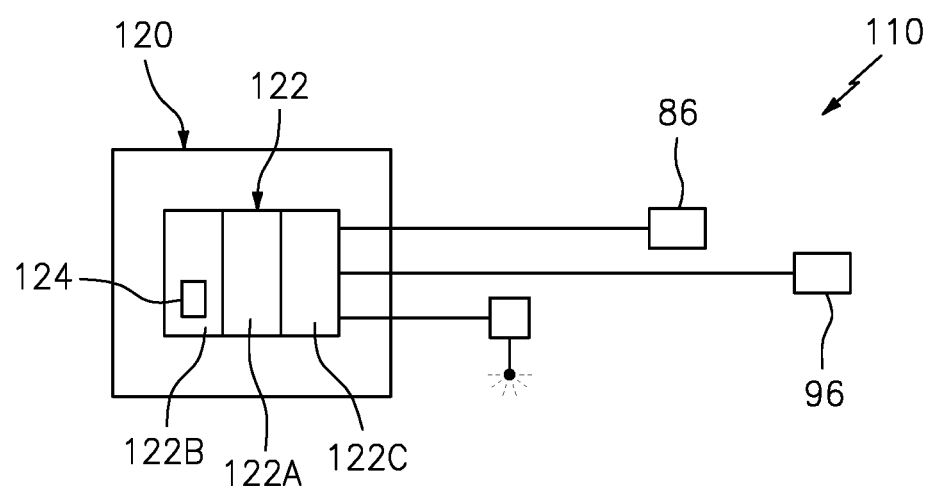
FIG. 4 is a schematic diagram of a debris management system according to one disclosed non-limiting embodiment.

With Reference to FIG. 4, a debris management system 110 generally includes a controller 120 in communication with the sensors 86, 96. The sensors 86, 96 may be in-line oil debris monitor sensors. The debris management system 110 protects against unexpected phase angle changes which may affect individual oil debris monitors caused by replacement or redesign of other components in the system, such as a signal wire harness, that can drastically influence the phase angle.

The controller 120 generally includes a control module 122 that executes logic 124 (FIG. 5) to actively calculate and monitor the oil debris monitor phase angle with regards to particle detection and system deterioration, stability and health. The functions of the logic 124 are disclosed in terms of functional block diagrams, and it should be appreciated that these functions may be enacted in either dedicated hardware circuitry or programmed software routines capable of execution in a microprocessor-based electronics control embodiment. In one example, the control module 122 may be a portion of a flight control computer, a portion of a Full Authority Digital Engine Control (FADEC), a stand-alone unit, or other system.

The control module 122 typically includes a processor 122A, a memory 122B, and an interface 122C. The processor 122A may be any type of known microprocessor having desired performance characteristics. The memory 122B may be any computer readable medium which stores data and control algorithms such as the logic 124 as described herein. The interface 122C facilitates communication with other components such as the sensors 86, 96, as well as remote systems such as a ground station, Health and Usage Monitoring Systems (HUMS), or other system.

The oil debris monitor phase angle is used to classify detected particle types (ferrous/nonferrous) through a mathematical transformation. The phase angle is calibrated by pulling a particle of known type and size through the sensor and using the ratio of I and Q channel amplitude and trigonometric relationships to calculate an optimum (for classification) phase angle. The I channel is the In-phase, or real component and the Q channel is the Quadrature (90° shift of real component). As will be further described below, this principle is applied to background noise in the system by calculating the slope of the relationship between noise peaks of the oil debris monitor I and Q data channels.

Figure 5:
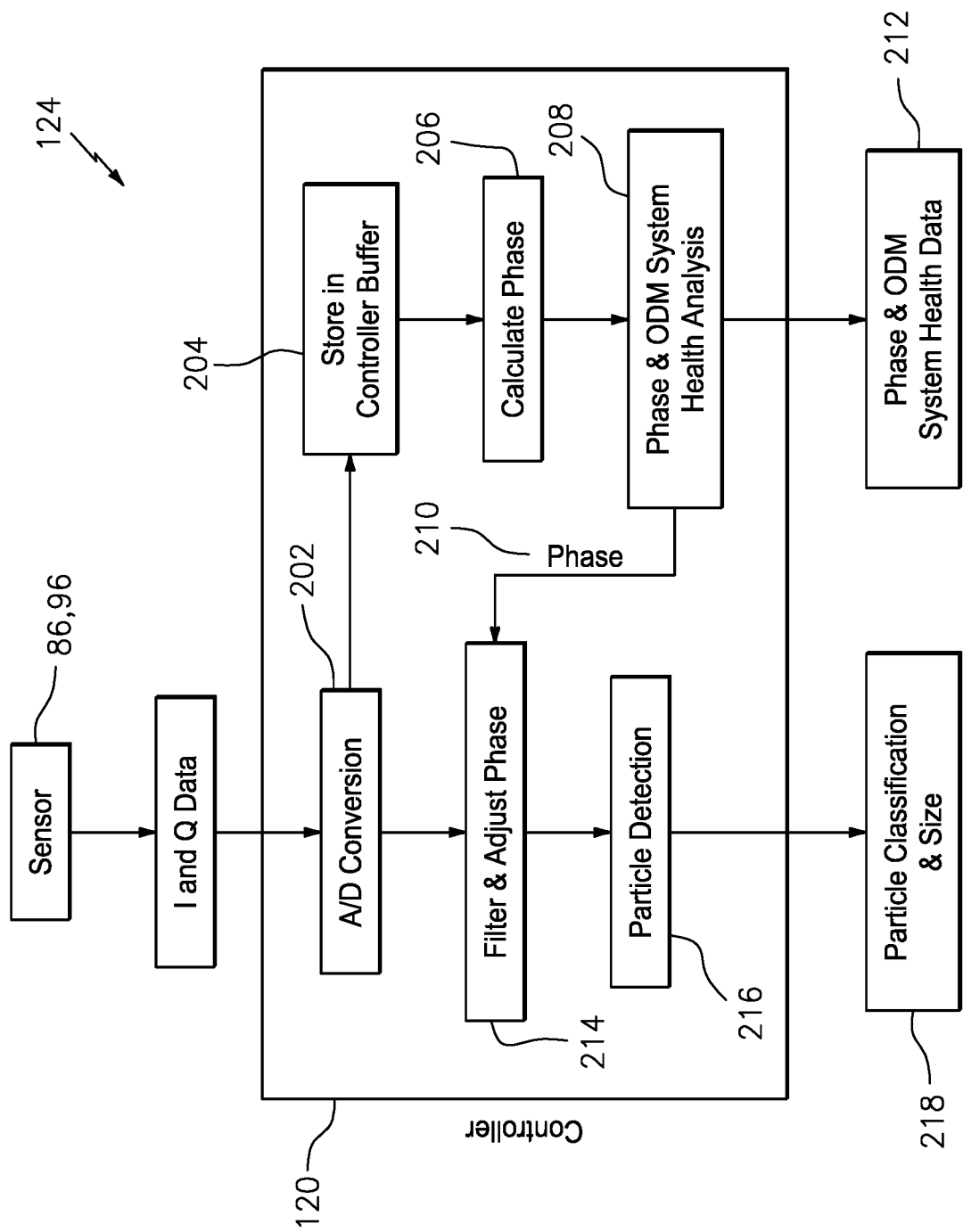
FIG. 5 is a block diagram representative of logic for the debris monitoring system.

With reference to FIG. 5, the logic 124 for particle analysis with the controller, initially includes receipt of raw oil debris monitor data from either or both of the sensors 86, 96 into the controller for signal conversion from analog to digital (202). The raw data is stored in a controller buffer (204). The buffer for the controller is continually filled with raw data that flows as a constant stream such that a running on-board calculation may be performed.

Figure 6:
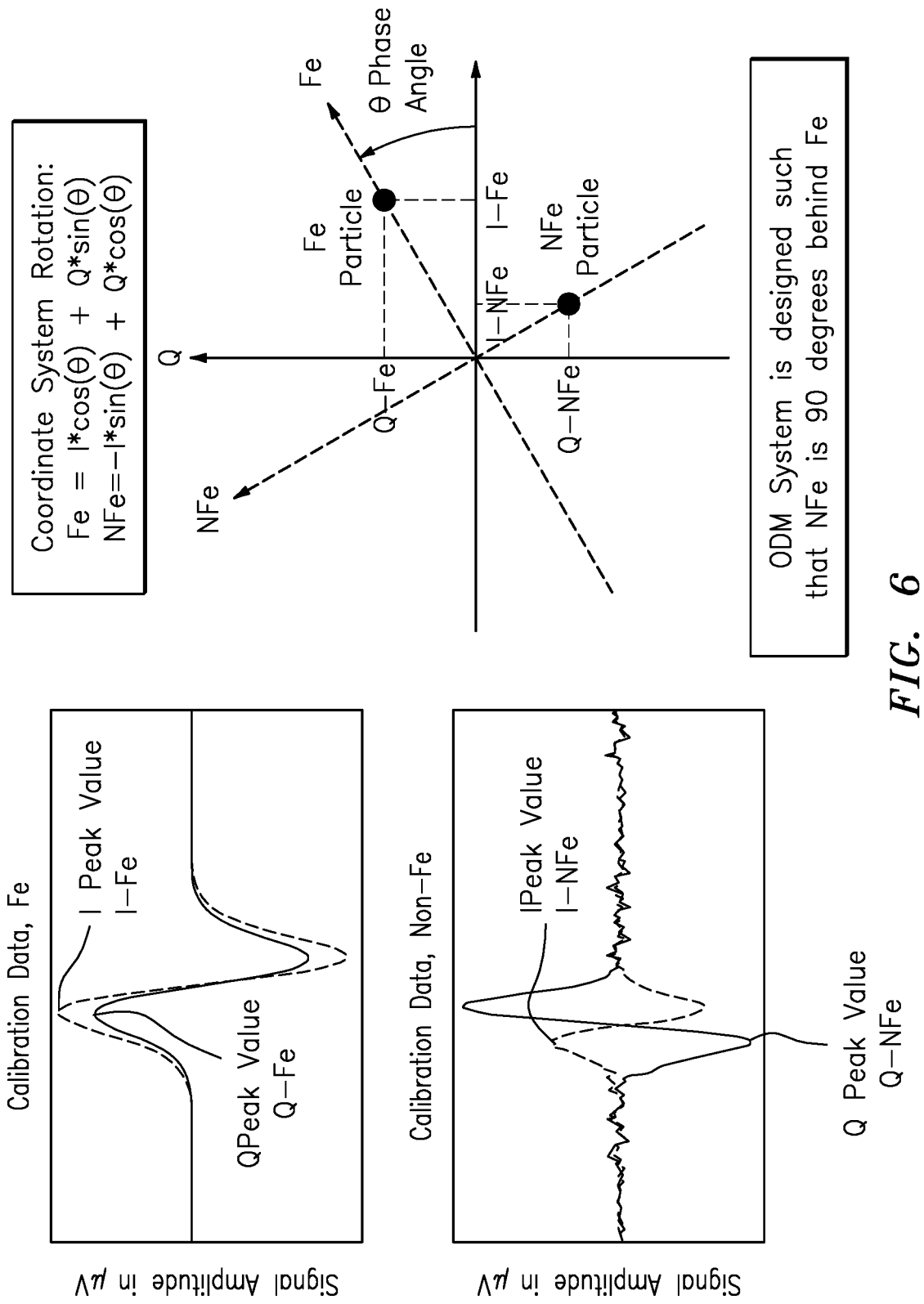
FIG. 6 is a schematic representation of a coordinate system to determine phase angle.
Figure 7:
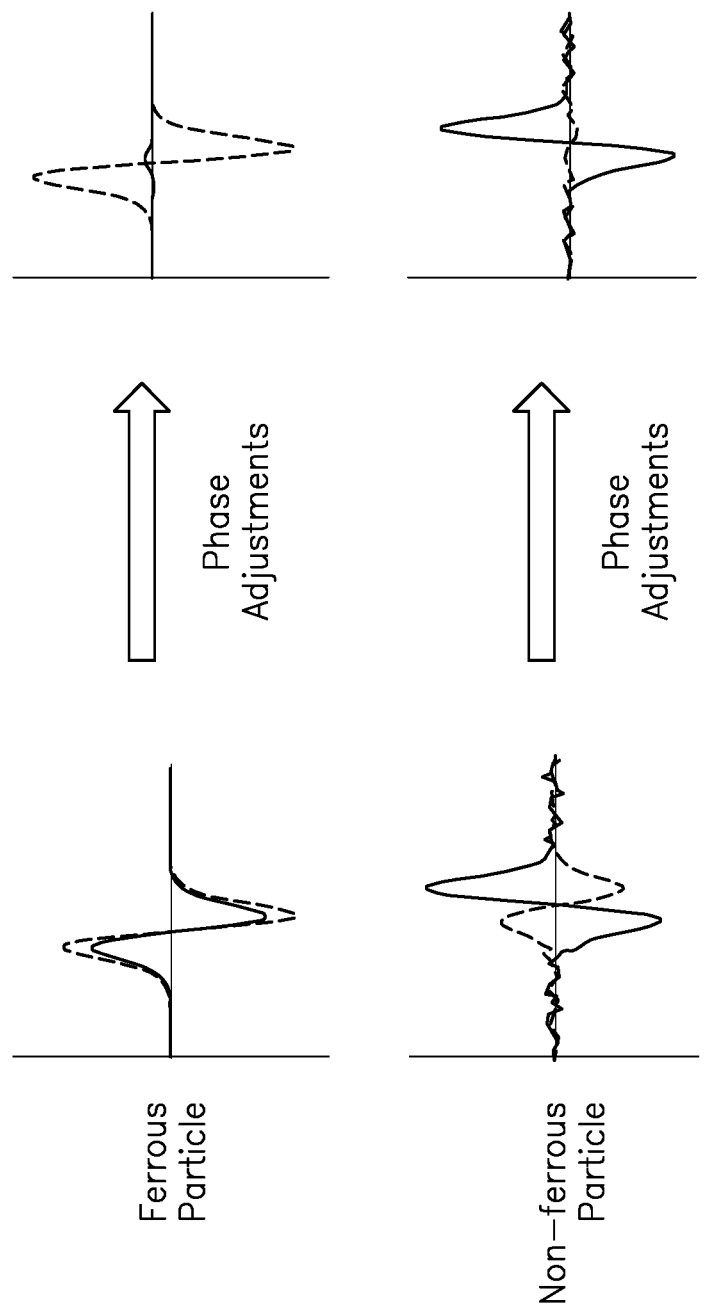
FIG. 7 is a graphical representation of a phase adjustment of the phase angle for a ferrous and nonferrous particle by the controller.

The phase angle of the signal (206; FIG. 6) is calculated from the noise using the raw oil debris monitor data in the controller buffer. The phase angle may then be used for a system health assessment (208) and may be transmitted (210) for further processing in the controller as well as transmitted with system health data for off-board health monitoring (212). The system health assessment may include, for example, particle count, particle type classification, size and mass estimates, system availability, debris count rates, and other metrics. The A/D converted raw oil debris monitor signals are filtered and phase angle adjusted (214) within the controller, then the particle detection algorithm executes (216). Typically, the particle signal will distribute into both I and Q channels due to phase angle misalignment between the drive signal and mixer signal as caused by system impedance in the driving and sensing circuitry. The phase angle adjustment (FIG. 7) realigns the particle signal distribution such that the ferrous particle signal is maximized in the ferrous channel and the nonferrous particle signal is maximized in then nonferrous channel. The particle classification and size data from the particle detection algorithm is then transmitted (218) for off-board health monitoring.

Figure 8:
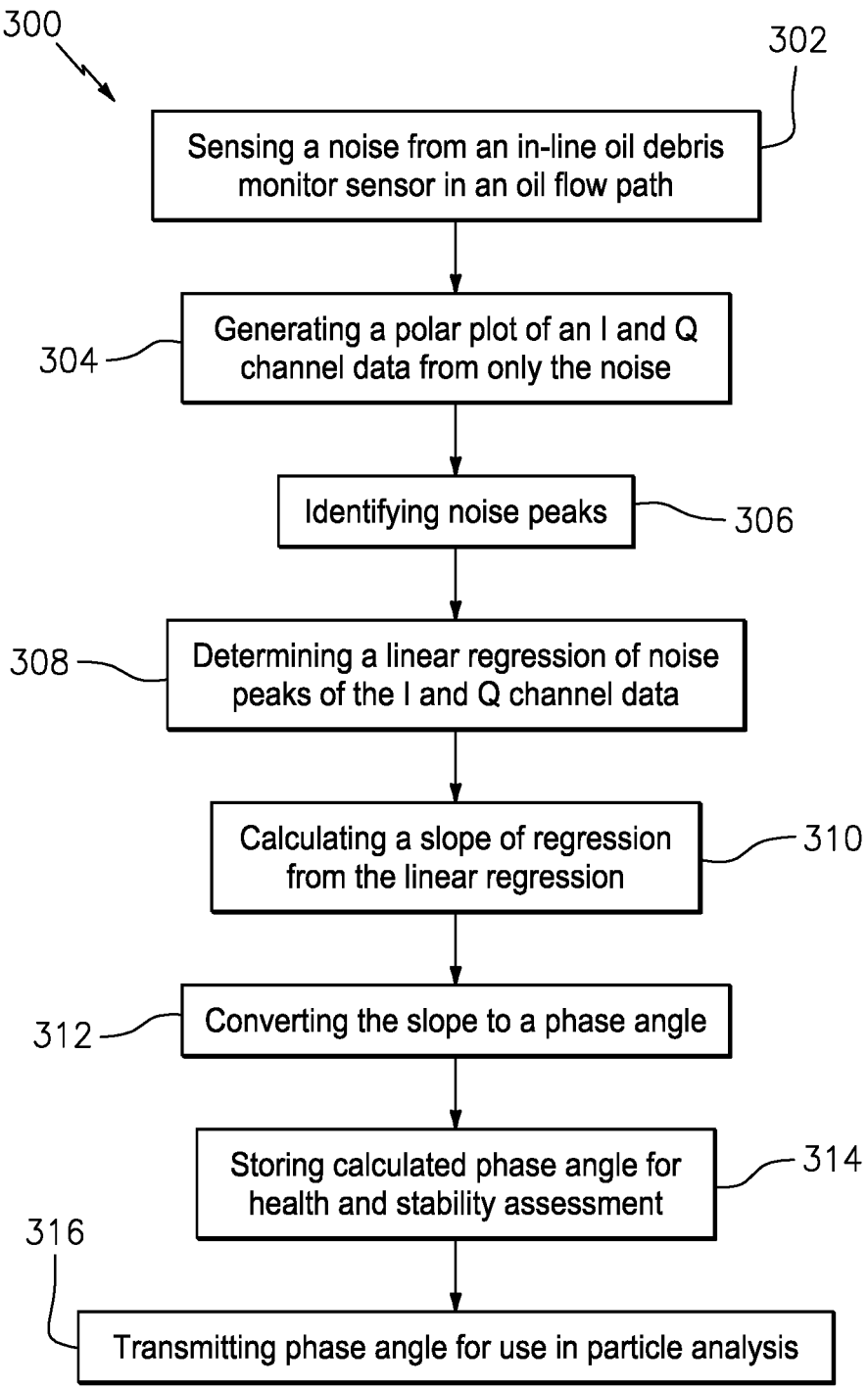
FIG. 8 is a block diagram representative of a method that calculate the phase as shown in FIG. 5.
Figure 9:
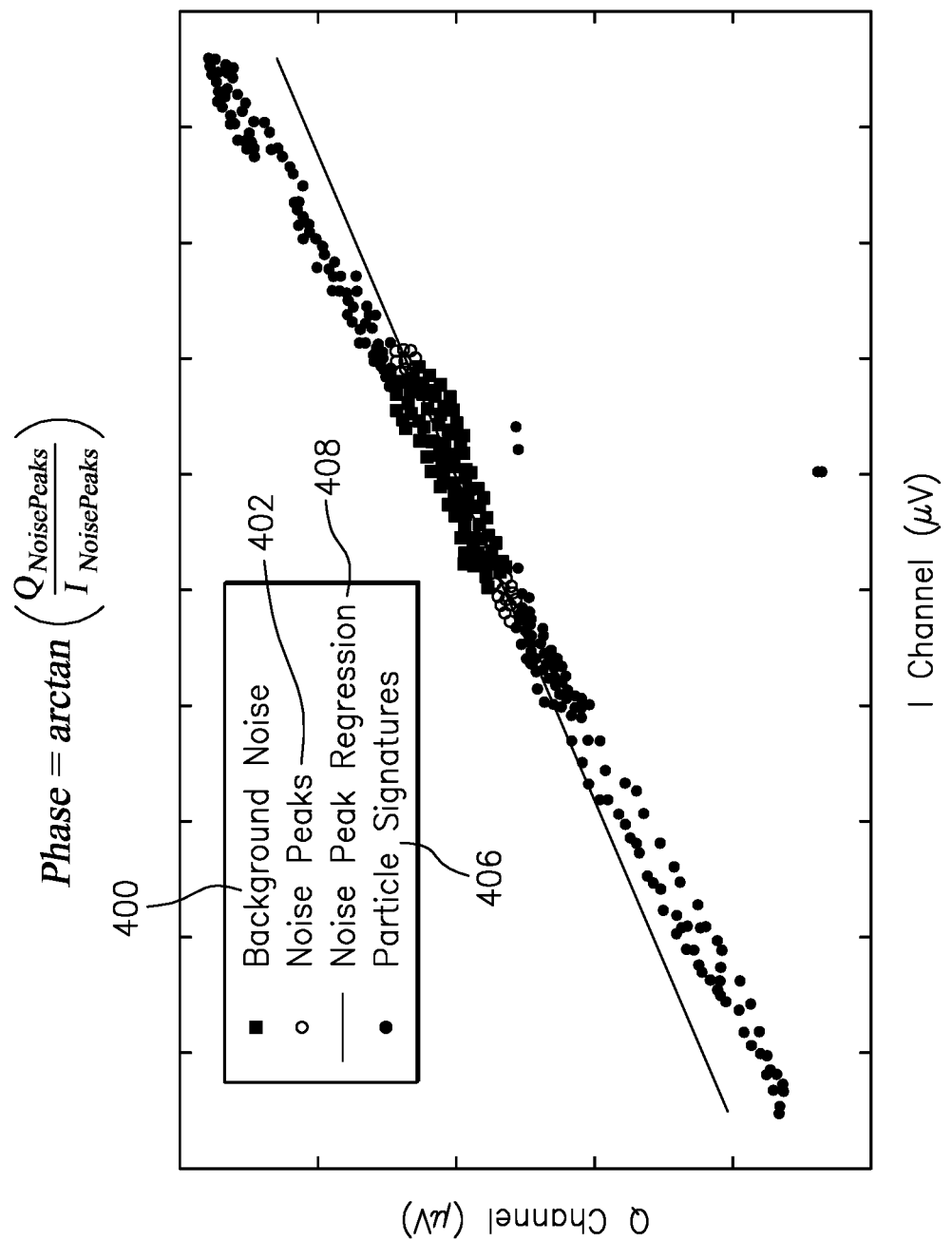
FIG. 9 is a graphical representation of a phase angle determination.

With reference to FIG. 9, a method 300 for actively calculating and monitoring the oil debris monitor phase angle on-board the controller initially includes accessing the oil debris monitor raw data from the controller buffer which has been obtained from the sensors 86, 96 (204; FIG. 5). Next, a polar plot of the I and Q data is created from the background noise 400 only (step 304; FIG. 9). Essentially, the noise 400 (FIG. 10) is isolated as compared to the particle signal 406 (FIG. 8) from actual particles.

Next, noise peaks (402; FIG. 9) which are the outer bounds of the polar plot are identified (step 306). Noise peaks are the outer bounds of the polar plot that may not be attributed to a particle.

Figures 10, 11, 12:
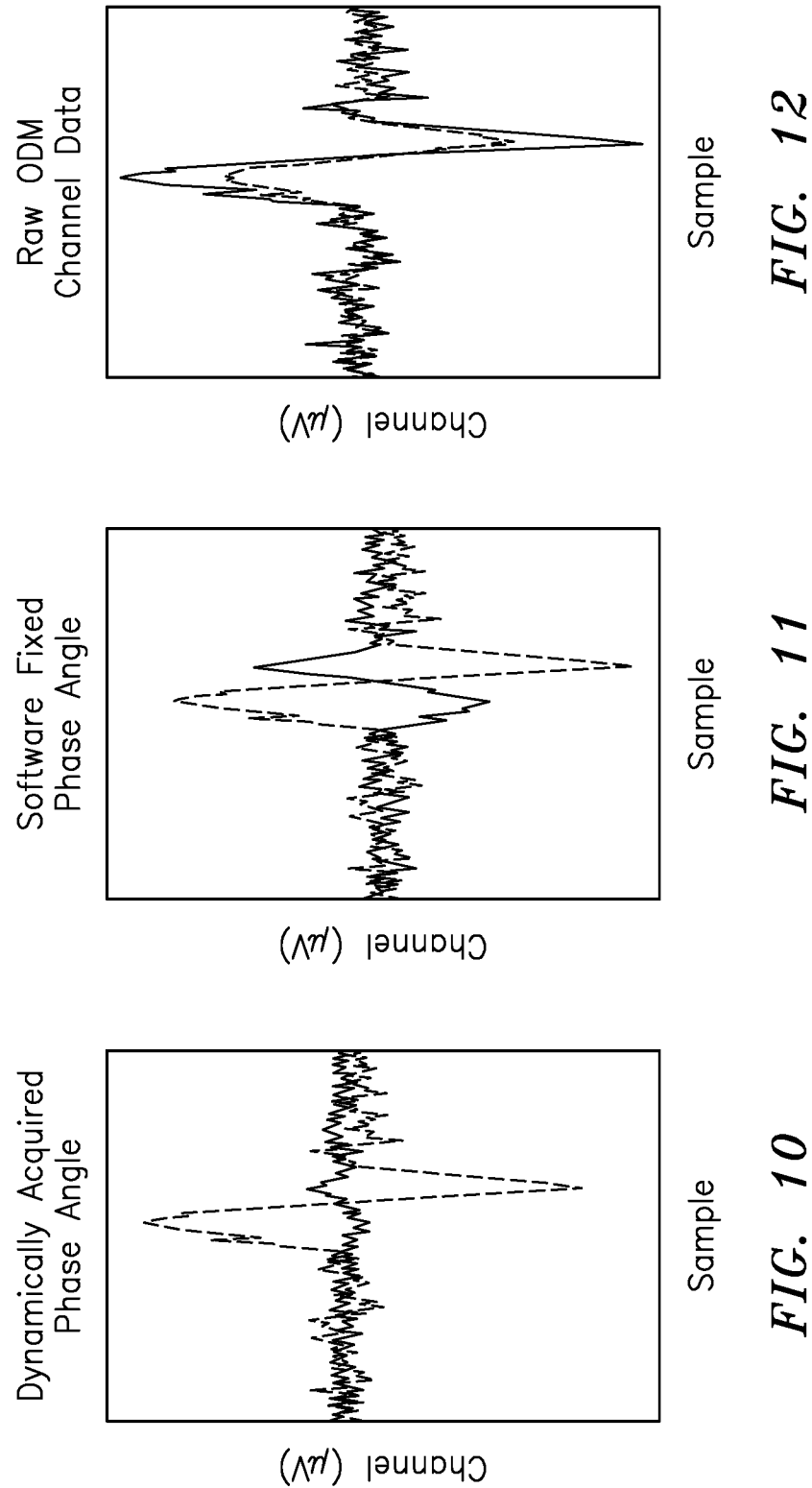
FIG. 10 is a graphical representation of a dynamically adjusted phase angle determination.
FIG. 11 is a graphical representation of a software fixed phase angle determination.
FIG. 12 is a graphical representation of raw ODM channel data.

A linear noise peak regression (408; FIG. 9) of the I and Q data noise peaks is then performed (step 308). The linear noise peak regression generates a line with a slope that is used to calculate phase. For example, linear regression may be utilized generally or specifically with the peaks. Next, a slope of linear noise peak regression is calculated (step 310) then converted to phase angle (step 312). The slope may be determined with the arc tan formula (FIG. 10). In current systems, the phase angle is a fixed value in the software based on calibration tests and peaks of the particles are utilized to calculate the phase angle. In contrast, by focusing on the noise, the phase angle is calculated in essentially real time. For example, the phase angle may be a calculated value that is about 125% (FIG. 10) compared to a software fixed value (FIG. 11) based on the same raw ODM channel data (FIG. 12). The noise provides a calculated phase angle to show the ferrous particle without any nonferrous excitation. For example, the planner plot shows the fixed phase angle of the system (FIG. 10) compared to use of noise feedback (FIG. 11).

Figure 13:
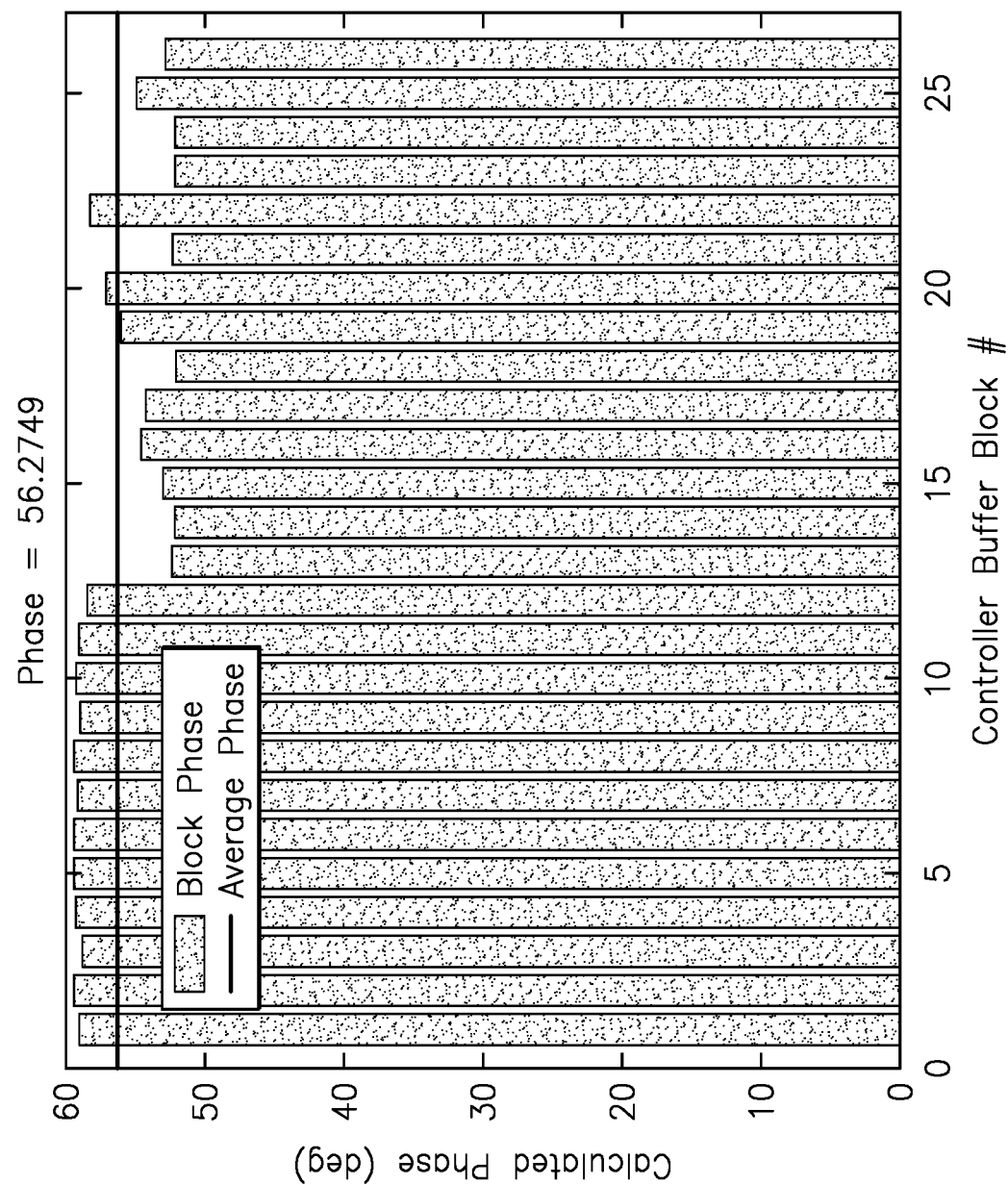
FIG. 13 is a graphical representation of a dynamically adjusted phase angle determination buffer in a stable condition as determined within the controller.

The calculated phase angle may then be stored (step 314) and/or transmitted (step 316) for health and stability assessment. The system is thus identified as healthy when the phase angle is stable (FIG. 13) compared to an unhealthy system that is not stable to provide another point for off-board trending.

Figure 14:
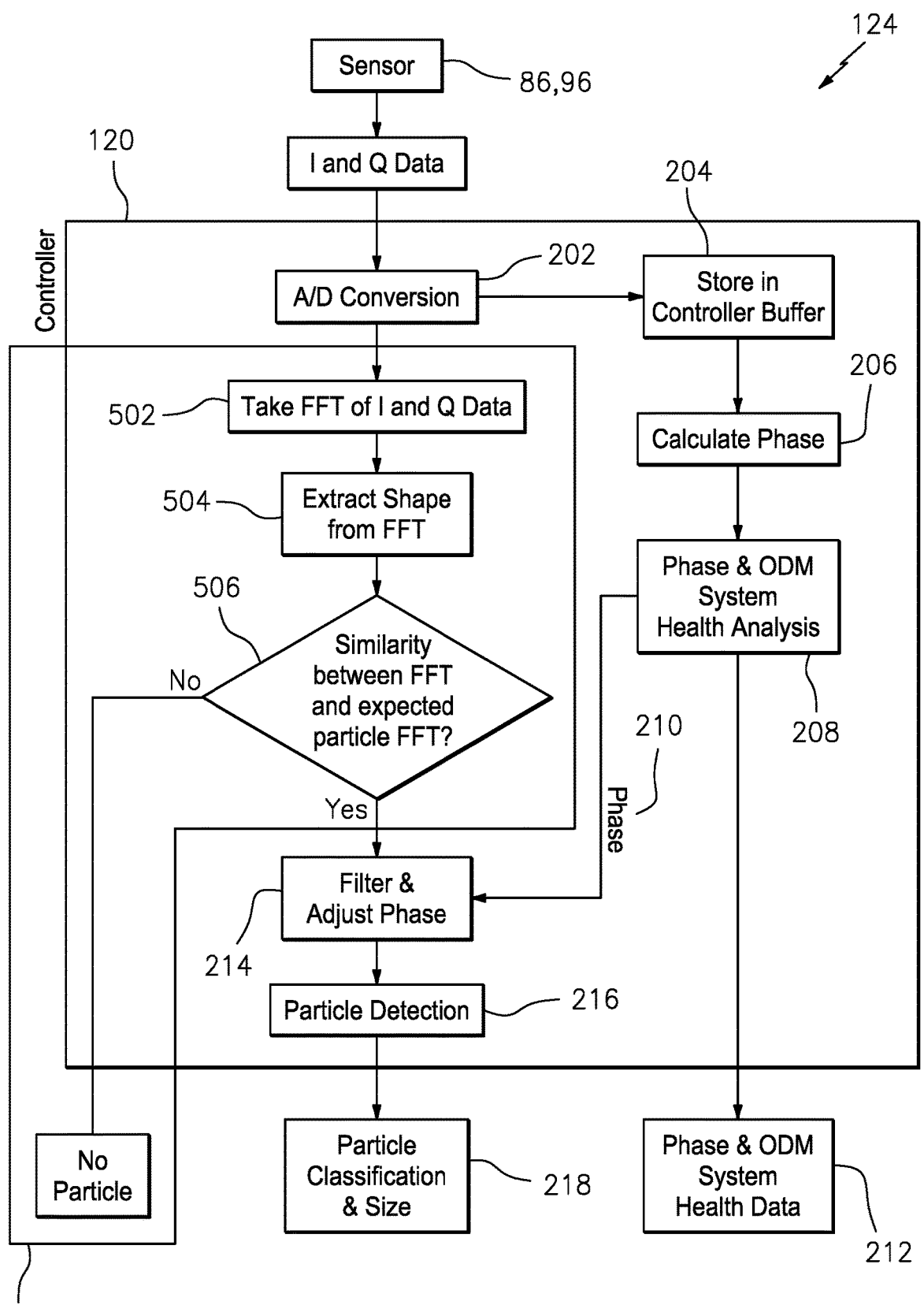
FIG. 14 is a block diagram representative of particle detection logic for the logic for the debris management system shown in FIG. 5.
Figure 16:
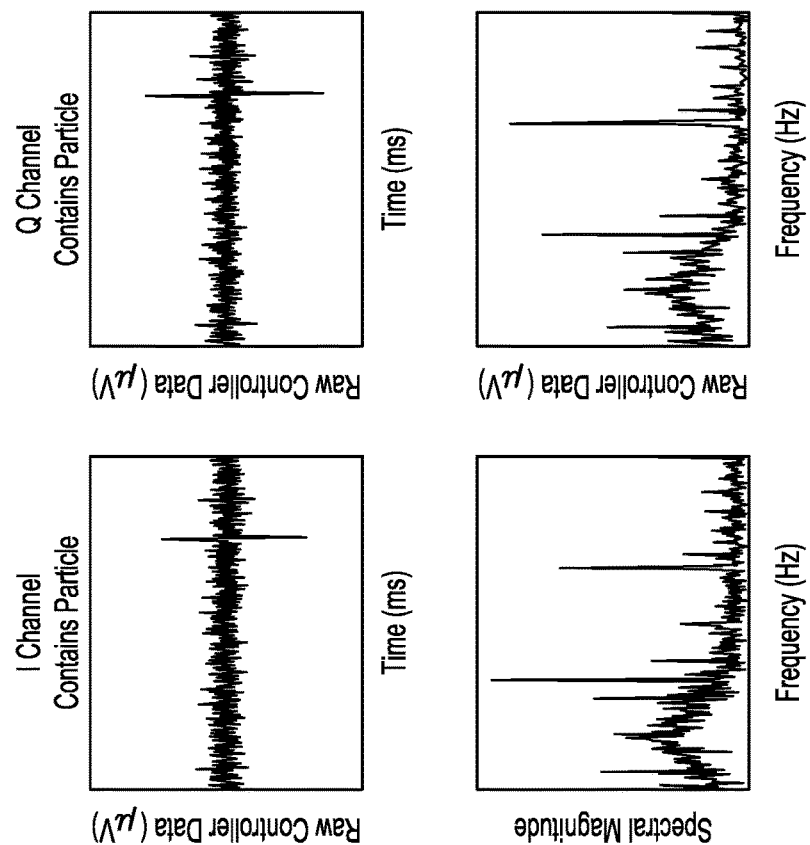
FIG. 16 is a graphical representation of the FFT of the controller buffer which contains a particle—note bow from 0 to 400 Hz peaked at 200 Hz.
Figure 15:
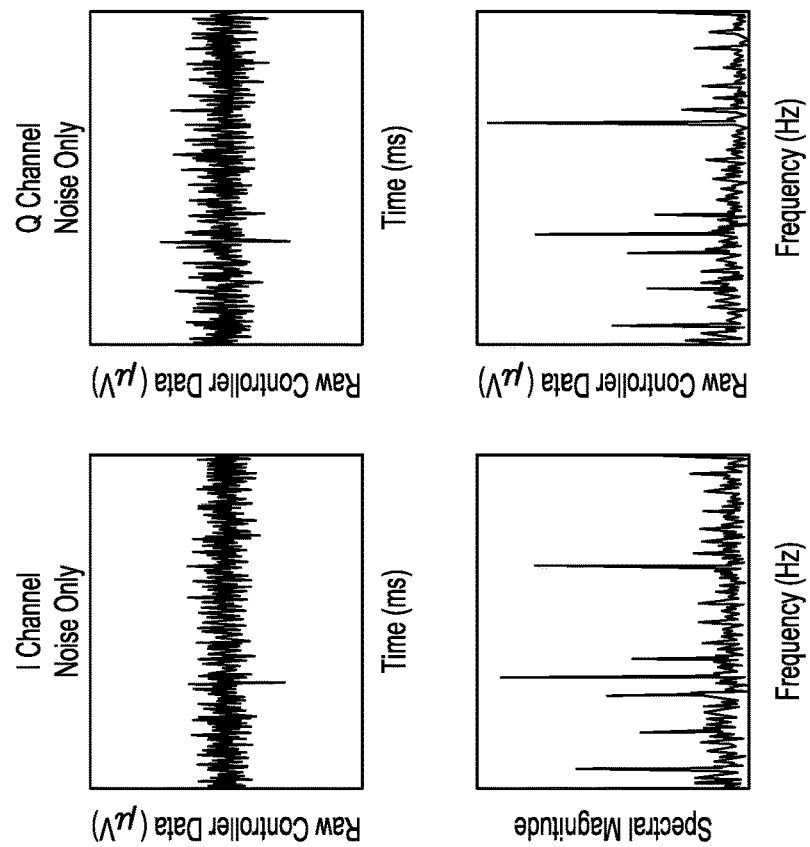
FIG. 15 is a graphical representation of the FFT of the controller buffer which contains only noise.

With reference to FIG. 14, the logic 124 for particle analysis (FIG. 5) with the controller 120 may, in another embodiment, include particle detection logic 500 via fast Fourier transforms (FFT) of the I and Q data stored in the controller buffer. The fast Fourier transform (FFT) is an algorithm that samples a signal over a period of time (or space) and divides it into its frequency components which are single sinusoidal oscillations at distinct frequencies each with their own amplitude and phase. The particle detection logic 500 provides an automated method to correctly assess particle characteristics that, even in a noisy system, can generate a particle count. The method will lead to rejection of signals that meet the requirements for a particle but do not have a particle shape, thus reducing false detections.

Figure 18:
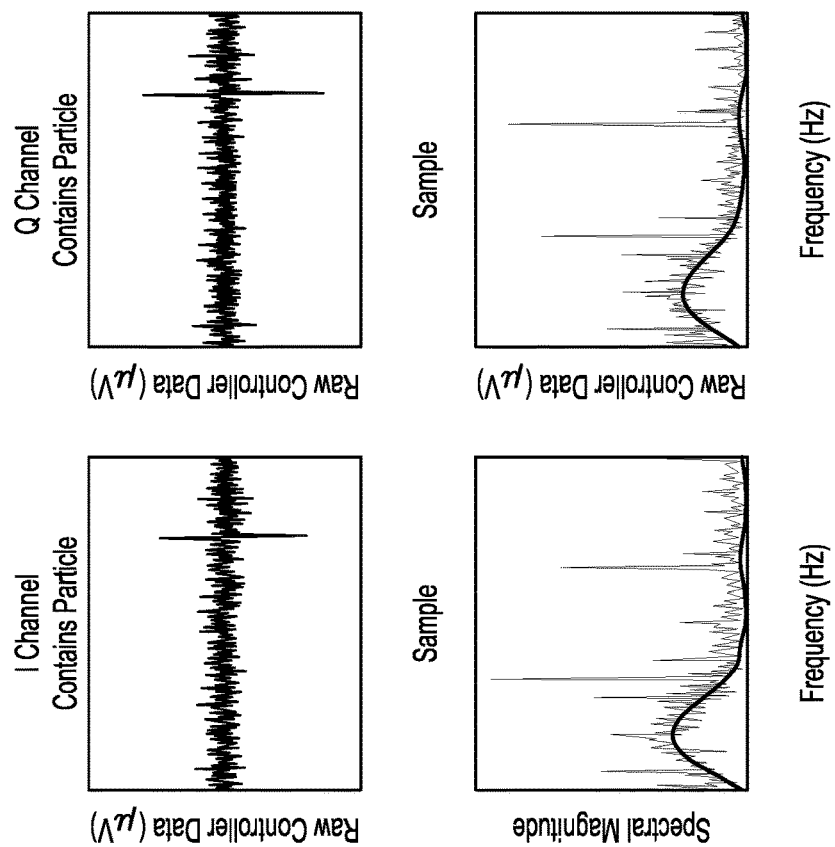
FIG. 18 is a graphical representation of the FFT of the 8192-pt. buffer containing particle overlaid with particle FFT.
Figure 17:
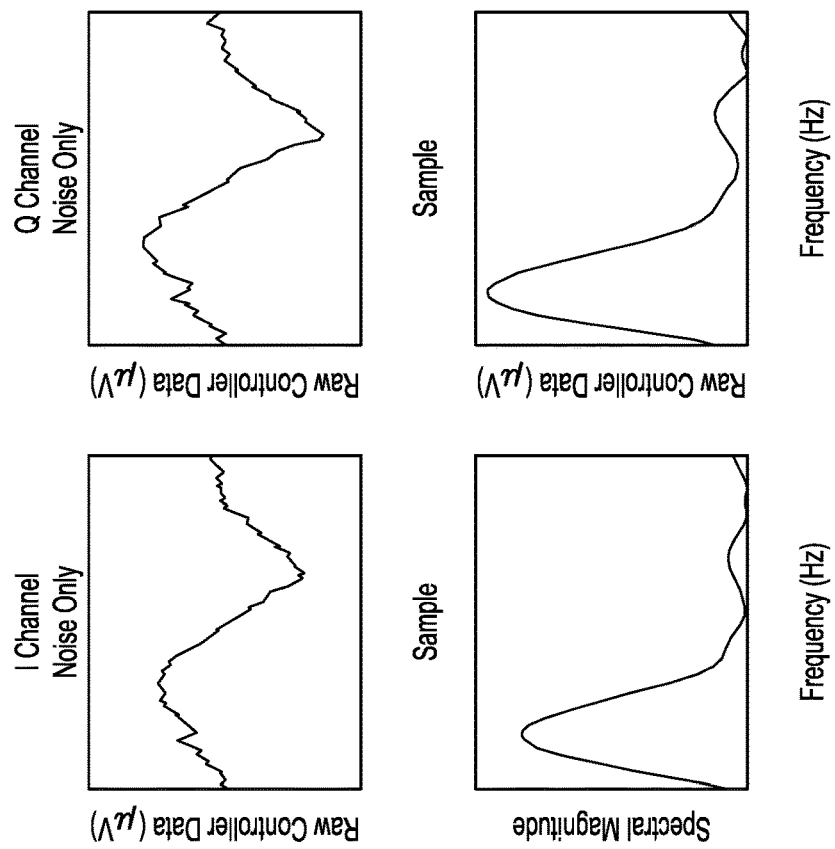
FIG. 17 is a graphical representation of the FFT of the particle alone scaled to 8192 pt. buffer.
Figure 20:
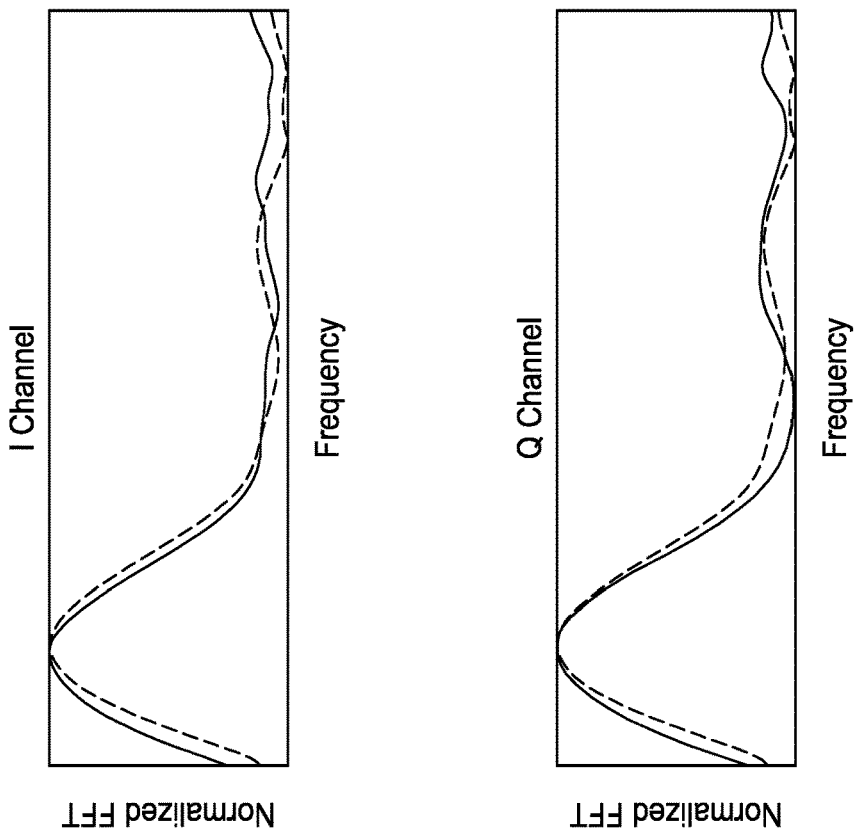
FIG. 20 is a graphical representation of the FFT of the particle alone vs. the FFT of particle containing buffer with the noise component removed.
Figure 19:
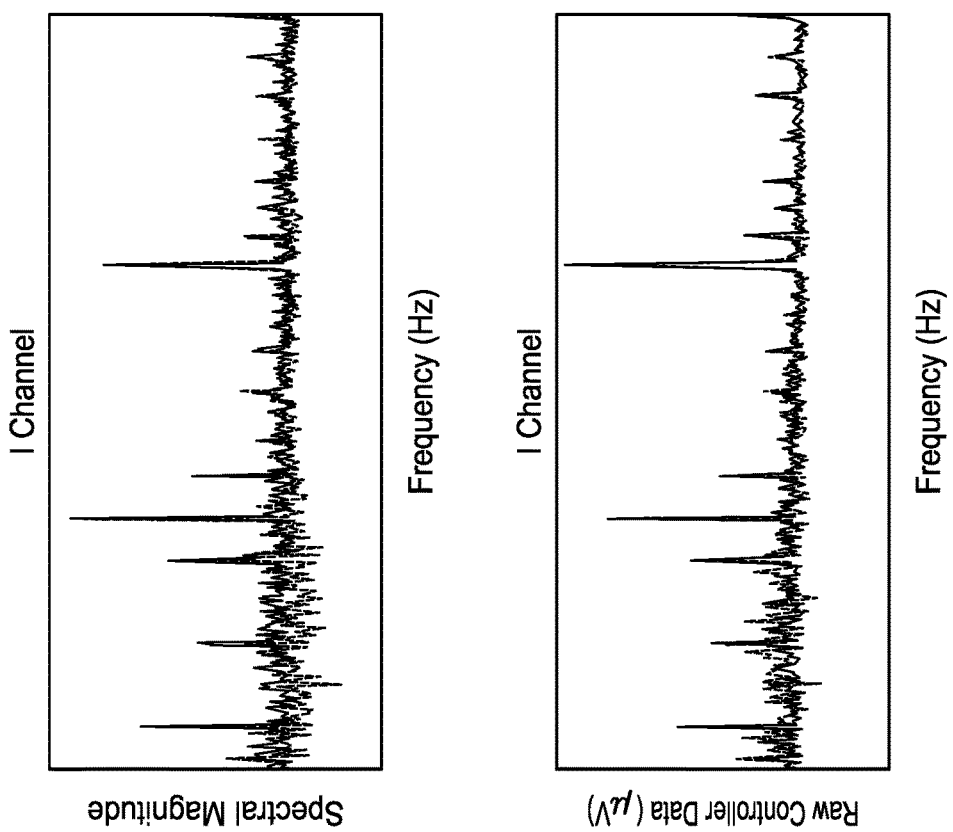
FIG. 19 is a graphical representation of the FFT containing a particle with the particle component removed compared to noise only FFT—note the FFT peaks are the same between buffer blocks after particle removal.

Initially, the particle detection logic 500 includes execution of FFT on the I and Q data (502). The resultant I and Q FFT data is then processed to extract an overall shape (504). The shape of the I and Q FFT data is then analyzed (506) and compared to a predetermined shape that represents the presence of a particle. The shape resulting from the I and Q FFT data may not be a perfect sinusoid but a bow shape (FIGS. 15-20). When comparing the FFT of the signal with no particle present (FIG. 15) to the FFT of the signal with a particle present (FIG. 16), the bow shape is identifiable. The FFT of the particle alone (FIG. 17) is responsible for the bow shape (FIG. 18). Removing the particle contribution of the FFT (FIG. 17) from the signal with the particle present (FIG. 16), it is observed that the resultant FFT is similar to (FIG. 15; FFT where no particle is present). More significantly, the smoothed and normalized FFT shape extracted (FIG. 16) can be mathematically compared to the particle FFT (FIG. 17) to identify similarity (FIG. 20). The I and Q FFT data in the buffer is analyzed for the predetermined shape at a predetermined range of frequencies representative of the oil flow rate.

If the difference between the particle I and Q FFT data and the particle removed I and Q FFT data is significant. The level of significance would vary based on applications. An example would be to use expected FFT shapes. At each frequency in the expected bow range (in this case 0 to 400 Hz), there is a maximum difference of, for example, +/−0.1, and the frequencies corresponding to the maximum of each bow is, for example, within 50 Hz], then it can be determined that a particle like signal exists. That is, if there is a shape similarity, the logic 124 continues as described above with respect to FIG. 5. If there is no shape similarity, the logic 124 for particle analysis is bypassed as no particle has been detected.

Figure 21:
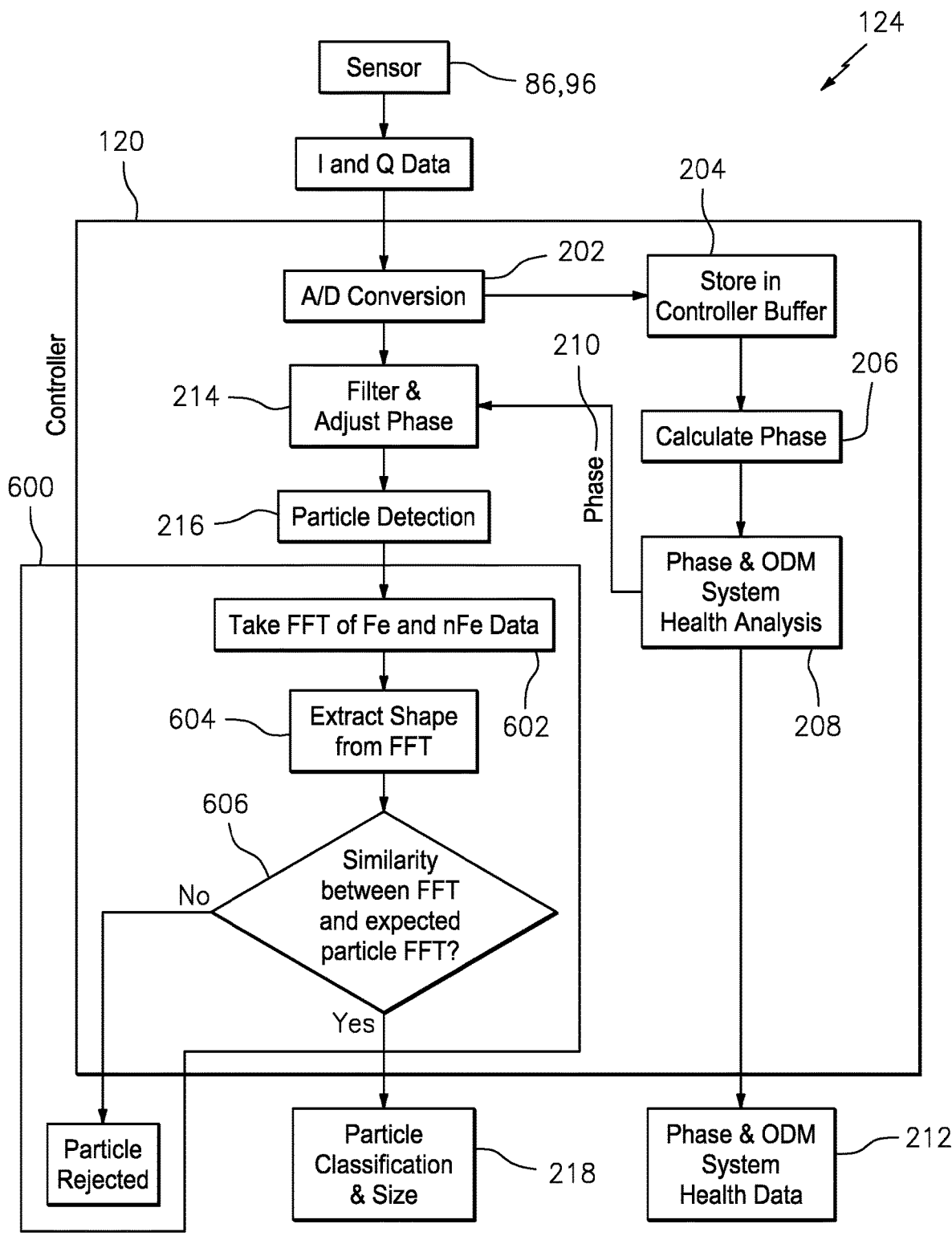
FIG. 21 is a block diagram representative of particle detection logic for the logic for the debris management system shown in FIG. 5.

With reference to FIG. 21, the logic 124 for particle analysis (FIG. 5) with the controller 120 may, in another embodiment, include particle rejection logic 600 via fast Fourier transforms (FFT) of the ferrous or nonferrous particle data after the particle detection algorithm executes (216; FIG. 5). To confirm that a true particle has been detected, the shape of the ferrous and nonferrous FFT data, the frequency center, and the lobe width requirements compared to that of a particle are checked. That is, the particle will typically produce a sinusoidal excitation on the ferrous and nonferrous data channel, and given the flow rates of the system and the range of frequencies that the shape covers, the detected particle is either accepted or rejected. An example of a rejected particle would be an electrical anomaly that is not a particle and visually is not particle like, but meets the symmetry, amplitude, and lobe width requirements in the software such as in the filter and phase adjustment stage.

Initially, the particle rejection logic 600 includes execution of FFT on the ferrous or nonferrous particle data (602). The resultant ferrous and nonferrous FFT data is then processed to extract the FFT shape (604). The shape of the ferrous or nonferrous particle FFT data is then analyzed (606) and compared to an expected shape. If there is a shape similarity, the logic 124 for particle analysis continues as described above with respect to FIG. 5. If there is no shape similarity, the particle is rejected from analysis by the logic 124.

Figure 22:
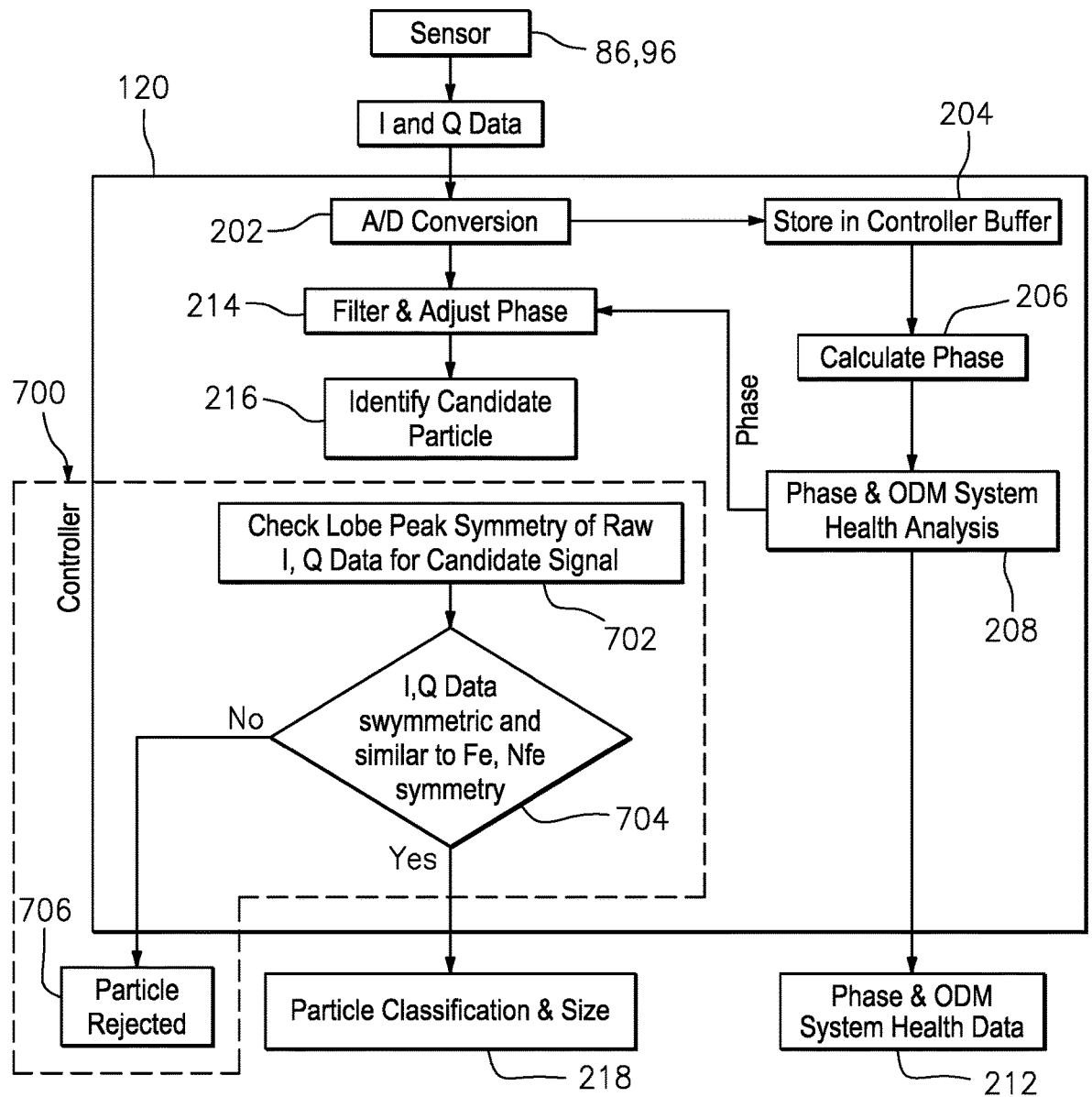
FIG. 22 is a block diagram representative of particle detection logic according to another embodiment for the logic for the debris management system shown in FIG. 5.

With reference to FIG. 22, the logic 124 for particle analysis (FIG. 5) with the controller 120 may, in another embodiment, include particle rejection logic 700 based on the understanding that a true particle signal is sinusoidal in nature with symmetric lobes. A processed (filtered and phase adjusted) ferrous/non-ferrous signal is utilized for particle detection. The particle will typically produce a sinusoidal excitation on the ferrous and nonferrous data channel, and given the flow rates of the system and the range of frequencies that the shape covers, the detected particle is then either accepted or rejected. An example of a rejected particle would be an electrical anomaly that is not a particle and visually is not particle like, but meets the symmetry, amplitude, and lobe width requirements in the software.

A processed (filtered and phase adjusted) ferrous/non-ferrous signal is exclusively utilized for particle detection and signal rejection. Initially, the particle rejection logic 700 uses the processed ferrous and nonferrous single coupled with output from the particle detection algorithm (216; FIG. 5) to disposition a candidate signal. The rejection logic may, for example, account for lobe and peak symmetry, and width, in the processed signal, but does not leverage critical information in the raw signal that is lost in the filtered and transformed ferrous and non-ferrous data. A true particle signal is sinusoidal in nature with symmetric lobes in the raw I, Q signal, and that symmetry is preserved in the transformed ferrous and non-ferrous signal. The filter and phase adjustment stage can convert a raw signal that does not meet symmetry requirements into a signal accepted as particle.

Next, the candidate signals proceed to a symmetry check (704). That is, the raw I and Q channel data is processed to confirm symmetry after the ferrous and nonferrous signal lobe peak symmetry (702) is confirmed. The symmetry check (704) compares the symmetry between the ferrous and nonferrous signals and the I and Q channel data to determine if the candidate signal is a particle. Utilizing the distorted ferrous and non-ferrous signal alone may lead to an invalid signal being accepted as a particle. The I and Q channel data itself, however, may not be particle like, and a symmetry check on this data can be utilized for rejection. In one embodiment, symmetry check (704) is performed via determination of a symmetry factor:

$$\text{Symmetry factor=peak/absolute value (valley)} \quad [1]$$

The example I and Q channel data (FIG. 23) is converted into ferrous and nonferrous signal data (FIG. 24). The ferrous and nonferrous signal data is processed and would incorrectly accept this signal as a particle. The raw I and Q channel data, however, is not particle like, and the symmetry check (704) on this data would result in rejection. For example, if the symmetry factor is greater than the threshold (e.g., 1-4 FIG. 25), the particle is rejected from analysis by the logic 124.

Input data (FIG. 26) is converted into the ferrous and nonferrous signal data (FIG. 27). The ferrous and nonferrous signal data is processed and would accept this signal as a particle. The raw I and Q data, however, is not relatively symmetric like a particle, so a symmetry check (704) on this data would result in rejection. For example, if the symmetry factor is greater than the threshold (e.g., 1-4 FIG. 28), the particle is rejected from analysis by the logic 124.

With reference to FIG. 29, the example I and Q channel data lobe peak symmetry (702) is confirmed and the lobes have similar symmetry as the processed ferrous and nonferrous signals used for detection (FIG. 30). That is, the symmetry check (704) on this data in accordance with the method 700 would result in acceptance. That is, the symmetry factor is below a predetermined threshold (e.g., 1-4; FIG. 31), the logic 124 for particle analysis continues as described above with respect to FIG. 5.

The logic 700 leverages the observation that, for a true particle detection, the raw signal and processed signal will have a similar, symmetric, sinusoidal shapes. When a candidate particle is identified, the raw signal is then checked for symmetry against the requirements and against the detected particle. The logic 700 will identify the cases where a non-symmetric, non-particle like signal is distorted into a symmetric shape that will be accepted by the state machine logic. The logic 700 provides an additional validity check for candidate particles and a measure of sensing system health. Adding this functionality on on-board software would both reduce the cost and burden associated with nuisance detection and aid with fault isolation. The current technology uses a state machine to process a filtered and phase adjusted ferrous and nonferrous signal derived from the raw I and Q channel data. The raw data is not used in current technology. The current technology can accepts noise due to a non-particle like signal that, with parallel processing of the raw I and Q data, could be rejected.

The method 300 dynamically identifies the effect of phase angle change and adopts the appropriate phase angle. The real time phase angle can be determined on-board and used to provide a more accurate particle size and classification to determine the health of the diagnostic system and also provide a prognostic tool for predicting the state of the system in the future. The particle detection logic 500 and the particle rejection logic 600 and/or 700 provide an automated, real time check of a candidate particle viability. This removes human analysis from data review and provides for on-board discretion, reducing time and expense of data review.

Although particular step sequences are shown, described, and claimed, it should be appreciated that steps may be performed in any order, separated or combined unless otherwise indicated and will still benefit from the present disclosure.

The foregoing description is exemplary rather than defined by the limitations within. Various non-limiting embodiments are disclosed herein; however, one of ordinary skill in the art would recognize that various modifications and variations in light of the above teachings will fall within the scope of the appended claims. It is therefore to be appreciated that within the scope of the appended claims, the disclosure may be practiced other than as specifically described. For that reason, the appended claims should be studied to determine true scope and content.

What is claimed:

1. A method for determining the presence of a particle while actively calculating and monitoring oil debris monitor phase angle in an oil system, comprising: a) collecting I and Q channel data from an oil debris monitor sensor; b) determining whether the I and Q channel data is symmetric; c) processing the I and Q channel data to identify a ferrous and nonferrous signal in response to the I and Q channel data being symmetric in step b); d) processing the ferrous and nonferrous signals to determine if the particle is present; e) determining a symmetry factor from the I and Q channel data in response to the particle present in step d); and f) confirming that the particle is present from the symmetry factor.

2. The method as recited in claim 1, wherein step b) comprises determining if lobe peaks are symmetric.

3. The method as recited in claim 1, wherein the ferrous and nonferrous signals are used for particle detection.

4. The method as recited in claim 1, wherein said step d) comprises filtering and phase adjusting the ferrous and nonferrous signals.

5. The method as recited in claim 1, further comprising continually filling a buffer of a controller with the I and Q channel data.

6. The method as recited in claim 1, further comprising converting the I and Q channel data to digital I and Q data within a controller on-board an aircraft.

7. The method as recited in claim 6, further comprising locating the oil debris monitor sensor within an oil supply path.

8. The method as recited in claim 6, further comprising locating the oil debris monitor sensor within an oil return path.

9. The method as recited in claim 1, wherein the symmetry factor=peak/absolute value of the I and Q channel data.

10. The method as recited in claim 9, wherein the particle is rejected in response to the symmetry factor being less than a threshold.

11. The method as recited in claim 10, wherein the threshold is between 1-4.

12. The method as recited in claim 9, wherein the symmetry factor is applied to the I channel data.

13. The method as recited in claim 9, wherein the symmetry factor is applied to the Q channel data.

14. An oil system for a gas turbine engine, comprising: an oil flow path; an in-line oil debris monitor sensor; and a control system in communication with the in-line oil debris monitor sensor to collect I and Q channel data from the oil debris monitor sensor; determine whether the I and Q channel data is symmetric; process the I and Q channel data to identify a ferrous and nonferrous signal in response to the I and Q channel data being symmetric; process the ferrous and nonferrous signals to determine if the particle is present; determine a symmetry factor from the I and Q channel data in response to the particle present; and confirm that the particle is present from the symmetry factor.

15. The system as recited in claim 14, wherein the oil flow path is in communication with a geared architecture of the gas turbine engine.

16. The system as recited in claim 14, wherein the oil flow path is an oil supply path.

17. The system as recited in claim 14, wherein the oil flow path is an oil return path.

18. The system as recited in claim 14, further comprising a chip collector within the oil flow path.

19. The system as recited in claim 14, wherein the control system comprises a controller.

* * * * *